(12) United States Patent
Zorn et al.

(10) Patent No.: US 7,344,248 B2
(45) Date of Patent: Mar. 18, 2008

(54) OPHTHALMOSCOPE

(75) Inventors: Wolfgang Zorn, Munich (DE); Werner Reis, Munich (DE); Ronald Spaltmann, Grassau (DE)

(73) Assignee: WILD Medtec GmbH, Vienna (AT)

( * ) Notice: Subject to any disclaimer, the term of this patent is extended or adjusted under 35 U.S.C. 154(b) by 958 days.

(21) Appl. No.: 10/478,844

(22) PCT Filed: May 24, 2002

(86) PCT No.: PCT/EP02/05762

§ 371 (c)(1),
(2), (4) Date: Nov. 24, 2003

(87) PCT Pub. No.: WO02/094088

PCT Pub. Date: Nov. 28, 2002

(65) Prior Publication Data

US 2004/0174498 A1    Sep. 9, 2004

(30) Foreign Application Priority Data

May 25, 2001  (DE) ................................ 101 25 596

(51) Int. Cl.
*A61B 3/10*    (2006.01)
*A61B 3/14*    (2006.01)
(52) U.S. Cl. ...................... 351/214; 351/205; 351/206; 351/221
(58) Field of Classification Search ................ 351/200, 351/201, 205, 206, 208, 210, 211, 214, 221
See application file for complete search history.

(56) References Cited

U.S. PATENT DOCUMENTS 5,371,557 A    12/1994    Nanjho et al.
5,841,509 A *  11/1998    Harooni et al. ............. 351/221
5,997,141 A    12/1999    Heacock

FOREIGN PATENT DOCUMENTS

DE          3714041 A1     11/1988
WO          WO97/15855      5/1977

* cited by examiner

*Primary Examiner*—Huy Mai
*Assistant Examiner*—Jack Dinh
(74) *Attorney, Agent, or Firm*—Buchanan Ingersoll & Rooney PC (57) ABSTRACT

The invention relates to an ophthalmoscope for examining the fundus of an eye of a patient, which comprises at least one illuminating device producing at least one illuminating beam, in addition to an imaging lens system which can be associated with the illuminating device and which images the illuminating beam onto the fundus of the eye of a patient; also comprising an observation device, wherein the imaging lens system images an observation beam onto the fundus of the eye, said observation beam being produced by reflecting the illuminating beam; also comprising a diaphragm arrangement introduced into the illuminating beam and the observation beam, whereby the gap of said diaphragm can be variably modified and synchronized. The invention is characterized in that the imaging lens system is formed in such a manner that an intermediate focal plane is created along the illuminating beam and the observation beam, wherein the fundus of the eye and the illuminating device are imaged, so that the intermediate focal plane is imaged infinitively, and so that the infinitively formed intermediate focal plane is imaged on an image plane of the observing beam, wherein the observation device is arranged.

38 Claims, 11 Drawing Sheets

FIG. 8A view DE

OPHTHALMOSCOPE

FIELD OF THE INVENTION

The present invention relates to an ophthalmoscope for examining the fundus of a patient's eye having at least one illumination means producing at least one illumination beam as well as an imaging optic which can be assigned to the illumination means and which images the illumination beam onto the fundus of the patient's eye via an intermediate focal plane. Furthermore, the ophthalmoscope has at least one observation means as well as an imaging optics which can be assigned to the observation means and which images an observation beam generated by reflection of the illumination beam on the fundus via the intermediate focal plane into the observation means. Finally provided in the illumination beam and the observation beam is a diaphragm arrangement having at least one diaphragm slit which can be introduced in the illumination beam and the observation beam respectively, the diaphragm arrangement being mounted in such a manner that it oscillates synchronously relative to the illumination beam and observation beam. Due to its oscillating diaphragm arrangement, which is placed in the observation beam path and the illumination beam path, such an ophthalmoscope arrangement is also called a scanning ophthalmoscope.

BACKGROUND OF THE INVENTION

A generic device is known from U.S. Pat. No. 3,547,512. Due to the slit-shaped diaphragms in the observation beam path and in the illumination beam path, only a small area of the fundus is illuminated and simultaneously observed. In order, nonetheless, to be able to examine a larger part of the fundus, the illumination diaphragm and the observation diaphragm are moved synchronously, whereby a part of the fundus is scanned. If the fundus is observed using a detector that demonstrates a certain inertia and the movement of the slit images of the diaphragms occurs repeatedly fast enough over the same part of the fundus the single images melt to a whole image of the scanned part of the fundus.

This device should, in particular, improve observing the eye through a cloudy respectively opaque eye lens by reducing generation and observation of stray light including the resulting glare. A real intermediate image of the retina is generated outside the eye by means of an ophthalmoscopic lens, with the illumination means and the magnifying optical system being focused onto the plane of this intermediate image.

However, satisfactory results cannot be obtained just by means of the previously described measures. U.S. Pat. No. 3,547,512 therefore utilizes additional diaphragms respectively mirrors which mask out half of the observation beam bundle respectively of the illumination beam bundle in such a manner that the observation beam bundle and the illumination beam bundle run separately with the exception of a small intersecting region of the plane of the object. Although the generated respectively observed stray light is successfully further decreased in this way, the light intensity and the obtainable resolution are greatly diminished due to the confines of the apertures of the observation beam bundle and of the illumination beam bundle.

WO 97/15855 describes another generic optical device which should permit contrast-free and glare-free examination of the fundus thereby making the finest details visible. With this device, too, the fundus is at least partially illuminated with an illumination beam and the light reflected at the fundus is imaged as an observation beam via an optical lens system into an intermediate focal plane from which the illumination beam is imaged via an eyepiece unit for further analysis. This prior art arrangement is designed for contrast enhancement in that light-intensive interfering parts of the radiation are selectively weakened in such a manner that light-weak interference phenomena are also detectable. However, an eyepiece optic is still required, because additional light beams cannot be coupled into the illumination beam path and the observation beam path without considerably interfering with the overall optical system.

SUMMARY OF THE INVENTION

The object of the present invention is to provide a more compact design of an ophthalmoscope with an oscillating diaphragm, thus to design a scanning ophthalmoscope in such a manner that it permits, using a simple optical setup, direct as possible imaging of the fundus onto an observation means and, in addition, permits coupling further light bundles into the optical setup of the ophthalmoscope without permanently impairing the optical system.

The solution to the object of the present invention is the subject matter of claim 1. Advantageous further embodiments of the invention are the subject matter of the subclaims and can be derived from the description with reference to the preferred embodiments.

A key element of the present invention is to further develop an ophthalmoscope according to the generic part of claim 1 in such a manner that the intermediate focal plane is imageable to infinity via at least one optical unit and that the intermediate focal plane imaged to infinity is imageable in an imaging plane of the observation beam in which the observation means is provided.

The idea behind the present invention is based on the selective use of an optical unit which images to infinity the intermediate focal plane, in which the to-be-examined fundus is imaged outside the eye with the aid of an optical imaging unit, preferably an ophthalmoscope lens, i.e. the observation beam path is conveyed into a parallel bundle of beams which is imaged via a single additional optical unit immediately into an imaging plane in which the observation means is located. This direct guidance of the observation beam path onto the observation means rules out any loss of light that would ensue using additional intermediate imaging optics including the related aberrations. This direct imaging of the observation beam onto the observation means, which is designed for example as a CCD sensor in a video camera, permits keeping the optical design of the ophthalmoscope quite small and using the ophthalmoscope itself as a handheld device or as an auxiliary module, for example, for a slit lamp.

With the aid of an optimally designed imaging optic, the entire light that is reflected for examination at the fundus can be imaged completely practically without any loss onto the corresponding detector area of the observation means via the imaging optic assigned to the observation path, thereby reducing the glare on the patient's eye considerably. The invented ophthalmoscope arrangement is especially suited as an observation means in the form of a video scanning ophthalmoscope in conjunction with a video camera.

Like the parallel observation beam path imaged to infinity, which as previously described is imaged onto the light-sensitive area of the observation means via a, preferably, multi-lens objective arrangement, the illumination beam path also is provided with such a parallel beam section, preferably running parallel to the above-mentioned parallel beam path section of the observation beam.

For this purpose, an illumination lens system, preferably in the form of a condenser system, is provided in the imaging optic of the illumination beam which images the light rays of the illumination means onto a uniformly lit area lying in the imaging plane of the observation means. The uniformly lit area is conveyed via a multi-lens objective arrangement into a parallel running beam bundle, which the optical unit that images the observation beam to infinity focuses in the intermediate focal plane and which is imaged on the fundus by means of the optical imaging unit downstream in the beam path.

In the parallel running beam section of both the observation beam path and the illumination beam path, which are spaced a minimal lateral distance from each other and are, in addition, disposed symmetrically to the optical axis of the optical unit, which images both beam paths into the intermediate focal plane, an additional beam path, such as for example a therapeutic laser beam, can be easily coupled into the illumination and/or observation beam path without any further optical impairment of the imaging properties of the ophthalmoscope. This opens an especially interesting degree of freedom with regard to a modular optical extension of the ophthalmoscope thereby making new diagnostic and/or treatment methods on a patient's eye possible.

Inserting additional beam paths or even optical elements in the parallel beam path of the observation beam and or illumination beam is uncritical even in cases in which the optical unit for imaging the intermediate focal plane to infinity is moved axially to the parallel running observation and illumination beam paths. A shift in axial direction of the optical unit can, for example, be carried out in order to offset aberrations of the to-be-examined eye, in this way at the same time altering the position of the focal point of the optical unit. Thus, regardless of the aberration of the to-be-examined eye, the intermediate focal plane is imaged to infinity. Fading in corresponding scale lines in the observation beam path permits conducting defined measurement of dimensions at the fundus even in the case of various aberrations. This is especially important for long-term documentations with reproducible examination results. This will be explained in detail with reference to the preferred embodiments.

Located immediately before the imaging plane of the lit area and before the observation means, which for example is designed as a COD sensor, is a diaphragm slit arrangement which is mounted in a oscillating manner and provides a diaphragm slit for the observation beam as well as a diaphragm slit for the illumination beam respectively and the two diaphragm slits interrupt respectively release the corresponding beam paths in a synchronously oscillating manner. The purpose of the diaphragm slit arrangement mounted in an oscillating manner is to obtain contrast sharp and reflection-free illumination and imaging of the fundus. In order to be able to conduct different methods of examination of the fundus, diaphragm slits of different widths have to be employed. For this purpose, the diaphragm arrangement is provided with at least two pairs of diaphragm slits, which have diaphragm slit widths of different dimensions. Corresponding dimensioning of the widths of the diaphragm slits and their oscillating behavior in relation to the illumination beam path and the observation beam path permits adapting and optimizing the illumination situation individually to the respective fundus measurement task at hand.

For example, angiographic examinations of the fundus require a greater amount of light than conventional fundus images do. For conducting, for instance, fluorescence angiography, wide diaphragm slits are provided which are moved in an oscillating manner with a low oscillation amplitude through the observation beam path and the illumination beam path. If, on the other hand, examinations are conducted of the fundus, much less illumination intensity is needed, which is obtained using a pair of diaphragm slits of smaller slit width. For further details see one of the preferred embodiments in the following.

Another possible treatment of the fundus concerns age-caused macula degeneration, which can be examined and treated with the greatest precision with the aid of the invented device. In order to find flaws in the retina, a fluorescence angiography, in particular indocyanine green angiography is conducted in which the dye deposited in the retina is optically excited with the aid of a suited infrared laser. This infrared laser beam is coupled into the illumination beam path of the ophthalmoscope via a suited light fiber optic and a beam splitter respectively a swing mirror without interfering with the remaining optical setup of the ophthalmoscope. Preferably, such a swing mirror is located between the collimator and the illumination means, which usually is designed as an adjustable halogen lamp. Depending on the application, halogen light or infrared light can be selectively coupled in along the illumination beam path. Similarly, an optical stop filter can be swung in the illumination beam path, preferably, along the beam section within which the intermediate focal plane is imaged to infinity in order to image the fundus illuminated, depending on the mode of irradiation, by the halogen lamp or by the fluorescent light coming from the fundus onto the observation unit. Following spatial detection of the to-be-treated sites on the retina, moreover, the beam of a therapeutic laser can be imaged on the fundus, preferably in the feeder vessels, for selective coagulation of the tiniest spots on the fundus. Provided for this purpose are various masks, which can be placed in the intermediate focal plane and borne together with the optical unit in a moveable manner in order for the image of the mask placed in the intermediate focal plane to be sharply imaged on the fundus of the to-be-treated eye if there is an aberration. Similarly, suited rear projectors, filters or line masks can be placed in the intermediate focal plane in order to precisely mark certain, defined areas of the fundus in advance.

In order to keep the dimensions of the invented ophthalmoscope as small and compact as possible, external laser beams can be coupled in most expediently in the region of the parallel beam path. By means of suited interfaces, external laser adapters can be employed detachable or as a handle if used as a handheld device. Preferably such laser adapters can be replaced quickly and simply by means of suited flange devices.

The ophthalmoscope designed according to the present invention also permits stereoscopic observation of the fundus by providing two spatially separate observation beam paths, which, either combined with two separate observation means or temporally separated via a corresponding optical provision in the respective observation beam paths, are imageable in periodic succession as a single image sequence on a single observation means.

Further advantageous properties are described in the following parts of the description with reference to the preferred embodiments.

BRIEF DESCRIPTION OF THE DRAWINGS

The present invention is described by way of example in the following using preferred embodiments with reference to the drawings without the intention of limiting the scope or spirit of the over all inventive idea.

DETAILED DESCRIPTION OF THE INVENTION

Figure 1:
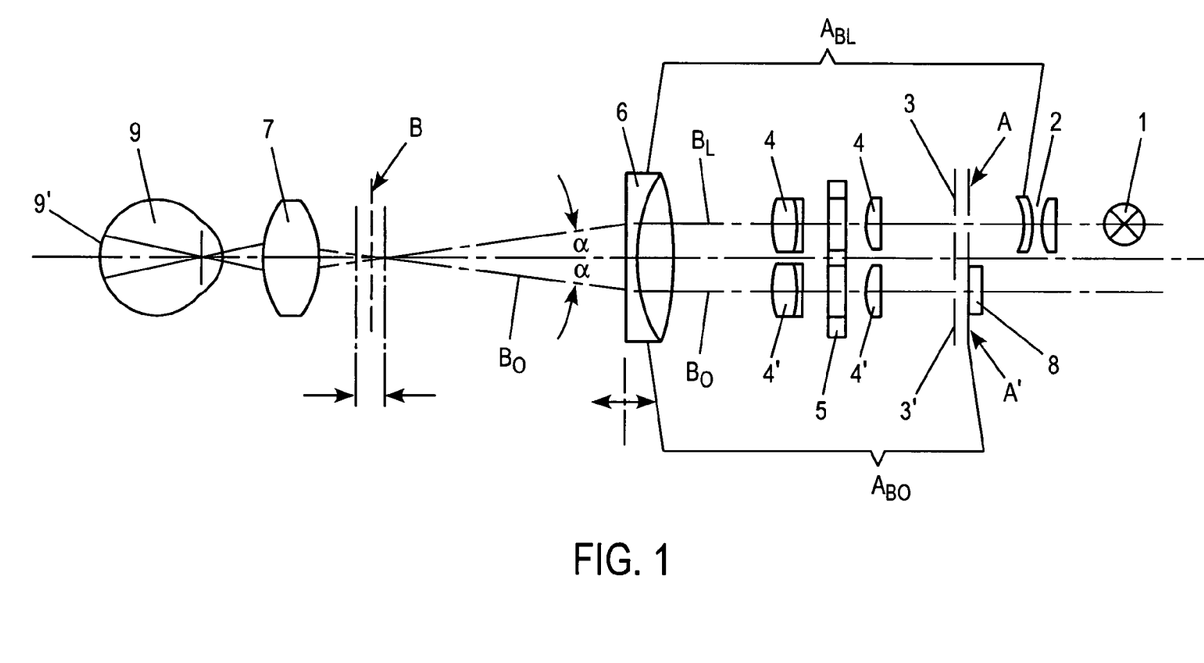
FIG. 1 shows a schematic representation of the beam paths of an invented indirect video ophthalmoscope with an exchangeable COD sensor.

FIG. 1 shows the basic optical setup of an ophthalmoscope designed according to the present invention.

Starting from an illumination means 1, which provides a halogen lamp as a light source, follows an imaging optic $A_{Bl}$ composed of a plurality of optical components assigned to the illumination beam Bl. The imaging optic $A_{Bl}$ comprising a condenser optic 2, which images the light of the halogen lamp 1 in a uniformly lit area in the imaging plane A, in which a diaphragm slit arrangement 3 is provided, which is mounted in a oscillating manner in relation to the illumination beam Bl, which will be dealt with in detail later. An optic unit 4 in the form of a multi-lens objective, which conveys the illumination beam Bl in a parallel beam, is provided behind the diaphragm slit arrangement 3 in the beam direction. The parallel illumination beam bundle is focused via an optical unit 6, which is provided with at least one achromat, into an intermediate focal plane B, from which the illumination beam is imaged on a patient's fundus 9' via an optical imaging unit 7, which preferably is designed as an ophthalmoscope lens.

The light coming from the illumination beam Bl is reflected at the fundus 9' and focused via the optical imaging unit 7 into the intermediate focal plane again in the beam direction converse to the illumination beam path. From the intermediate focal plane, the light is imaged via the imaging optic $A_{Bo}$, which comprises a plurality of optical components and is assigned to the observation beam path Bo of the ophthaloscope, onto an observation means 8 in the form of a CCD sensor in the following manner.

Starting from the intermediate focal plane B, in which the observation beam Bo coming from the fundus 9' is focused, the observation beam Bo reaches the optical unit 6, which simultaneously conveys the observation beam Bo in a parallel beam bundle and which simultaneously serves as an imaging means for the illumination beam Bl. In this manner, the optical unit 6 serves to image the intermediate focal plane B to infinity. Following downstream in the observation beam path, an optical unit 4' is provided, which is designed as a multi-lens objective and serves to immediately image the observation beam Bo in the imaging plane A', in which the light-sensitive detector area of the observation means 8 is located. Also provided in the observation beam path Bo between the optic unit 4' and the observation means 8 is a slit of the diaphragm slit arrangement 3', which, like the diaphragm slit in the illumination beam path, is mounted in an oscillating manner. The diaphragm arrangement 3,3' is preferably, as will be described in detail later on, designed as a pair of diaphragm slits which oscillates synchronously in the illumination beam path and the observation beam path.

Provided in combination with the optic units 4,4' is a filter arrangement 5, which is removably insertable in the respective beam paths of the observation beam and the illumination beam. The lateral space between the illumination beam path and the observation beam path is selected very small particularly in the region of the beam section in which the intermediate focal plane B is imaged to infinity and thus the respective beam paths are provided with parallel beam bundles in order, on the one hand to design the optical setup as small and compact as possible and, on the other hand, to realize the imaging of both beam paths with the aid of only a single optical unit 6 designed as a front lens. In this manner, a possible aberration of the to-be-treated eye of the patient can be offset by moving the optical unit 6 axially in relation to the common optical axis A of the illumination beam path and of the observation beam path. Usually the moving region of the optical unit 6 can be selected on both sides to a norm position in such a manner that the aberrations of ±15 dpt can be compensated. The aberration can be preset in a defined manner with the aid of a dioptric scale, not shown in FIG. 1, which for example is insertable in the intermediate focal plane B.

As the optical imaging unit 7 designed as an ophthalmoscope lens and the optical unit 6 are both passed through by the illumination beam path as well as by the observation beam path, due to the symmetrical beam guidance, the observation imaging plane A', in which the light-sensitive detector area, for example a COD sensor, of the observation means 8 is located, and the illumination imaging plane A, which appears as a uniformly lit area, are jointly imaged on the fundus 9' of the to-be-examined eye 9 and brought to concur.

For glare-free and reflection-free observation of the fundus with the aid of the ophthalmoscope depicted in FIG. 1, diaphragm slits, which are provided in the illumination beam path and the observation beam path respectively, are moved synchronously with each other in an oscillating manner relative to the illumination beam and the observation beam. In this way, the illumination beam path and the observation beam path are interrupted synchronously in such a manner that single, short shots of the lit fundus can be taken. However, each single shot only contains a part of the fundus. The position and size of the part depends on the respective width of the diaphragm slits, which is selected identical for both diaphragm slits in the observation beam path and the illumination beam path, as well as on the respective current position of the slits in relation to the illumination beam path and the observation beam path.

Fundamentally, all the components of the ophthalmoscope depicted in FIG. 1 can be replaced and attuned to each other depending on the desired recording conditions of the fundus. In particular, the optical imaging unit 7 designed as an ophthalmoscope lens can be replaced along with the optical unit 6 in order to obtain a desired image angle of the fundus. The observation means 8 can also be replaced by means of a corresponding easily detachable flange structure with an alternative observation means. Thus, for example, color cameras can easily be exchanged with highly sensitive black-and-white cameras, for example for taking fluorescent angiograms. In this connection, it is also advantageous to select and adapt the diaphragm arrangement 3,3' corresponding to the camera employed, in particular to the area size of the light-sensitive detector unit. Thus, for example, in conducting fluorescent angiography, larger slit widths are required than is the case with conventional examinations of the fundus.

Figure 2:
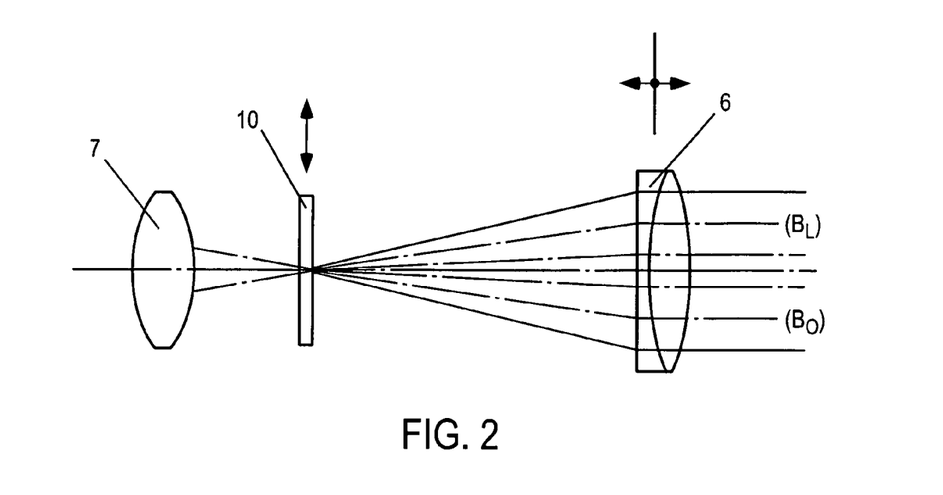
FIG. 2 shows an optical lens system of a beam path section having exchangeable optical components in the intermediate focal plane of the ophthalmoscope lens.

FIG. 2 shows a section of the beam path of the ophthalmoscope comprising an optical imaging unit 7 designed as an ophthalmoscope lens, an optical component group 10 which is randomly insertable respectively replaceable in the intermediate focal plane B and the axially movable optical unit 6 through which both the illumination beam path (Bl) and the observation beam path (Bo) pass. The replacable component group 10 comprises, for example, a stationary glass plate with no markings, a replaceable glass plate with markings or scales, a filter component group, a replaceable mask, for example for certain delimited irradiation areas on the retina, a rear slide projector, which also serves to preselect certain to-be-irradiated areas on the fundus for irradiation, or a dioptric scale. Preferably the optical component group 10 is coupled mechanically to the optical unit 9 in such a manner that it is mounted jointly moveable in longitudinal direction in the axial direction in order to set the aberration of the to-be-treated eye.

Figures 3A, 3B:
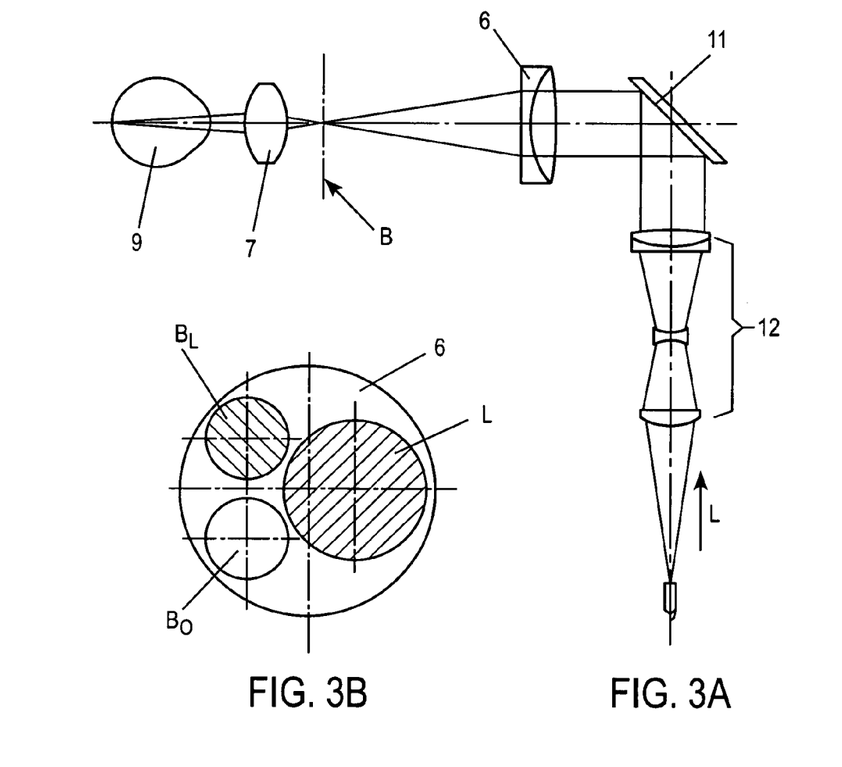
FIG. 3a shows a schematic representation of the reflecting in of a therapeutic laser.
FIG. 3b shows a schematic cross-section of the reflecting in of a therapeutic laser with an illumination beam path and an observation beam path.

FIG. 3a shows a schematic representation of a part of a beam path of the ophthalmoscope designed according to the present invention with reflecting in of a therapeutic laser. To extend the field of application of the indirect video ophthalmoscope, coupling in a therapeutic laser 12 is permitted via an additional deflection optic, for example in the form of a mirror 11. In an advantageous manner, the coupling-in element 11 designed as a mirror is located before the optical unit 6 in the beam direction of the illumination beam path Bl, thus in the region in which the illumination beam path and the observation beam path are parallel beam bundles. In this manner, the focal point of the therapeutic laser generated by the optical unit 6 always reaches the intermediate focal plane B independent of the current axial position of the optical unit 6. The size of the laser spot imaging on the fundus can adapt itself via a corresponding focussing optic, which is given by the imaging properties of the optical imaging unit 7 and the imaging conditions of the eye.

To change the spatial position of the laser spot imaged on the fundus, the deflection mirror 11 is preferably mounted movable in the X and Y direction in the form of a scanning mirror.

To make the ophthalmoscope more operation friendly, the therapeutic laser 12 can be designed as an adapter unit in such a manner that the therapeutic laser is attachable via a suited interface of a quick acting connection provided on the casing of the ophthalmoscope. For example a handle which can be replaced with a therapeutic adapter can be attached to this interface.

FIG. 3b shows a sectional drawing through the individual beam paths in the region of the intermediate focal plane imaged to infinity. This view shows the separation of the single beam paths, i.e. of the illumination beam path (Bl), the observation beam path (Bo) and the therapeutic laser beam path (L), distinctly. The single beam paths are imaged jointly via the optical unit 6 on the fundus via the intermediate focal plane B and the optical imaging unit 7.

Figure 4:
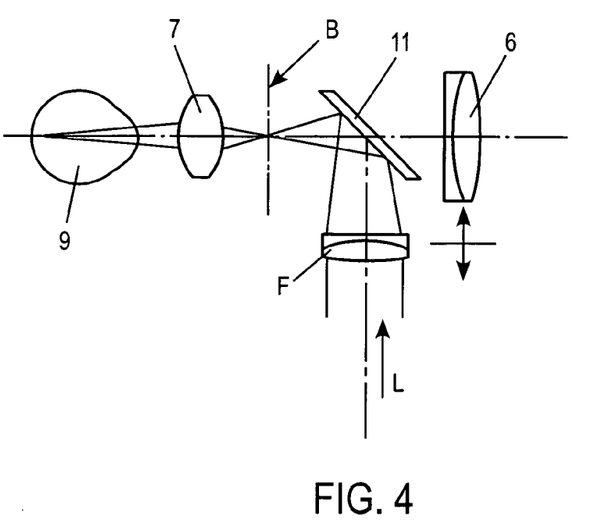
FIG. 4 shows a representation of the reflecting in of a laser before the ophthalmoscope lens.

FIG. 4 shows a preferred embodiment of a part of the ophthalmoscope in which coupling in of the therapeutic laser occurs between the intermediate focal plane B and the optical unit 6. By correspondingly changing the position of the optical unit 6 to adapt to the aberration of the to-be-treated eye 9, it is necessary to ensure that the focal point of the therapeutic laser beam is suitably corrected. This occurs in the preferred embodiment shown in FIG. 4 with the aid of a focussing lens F.

Figure 5:
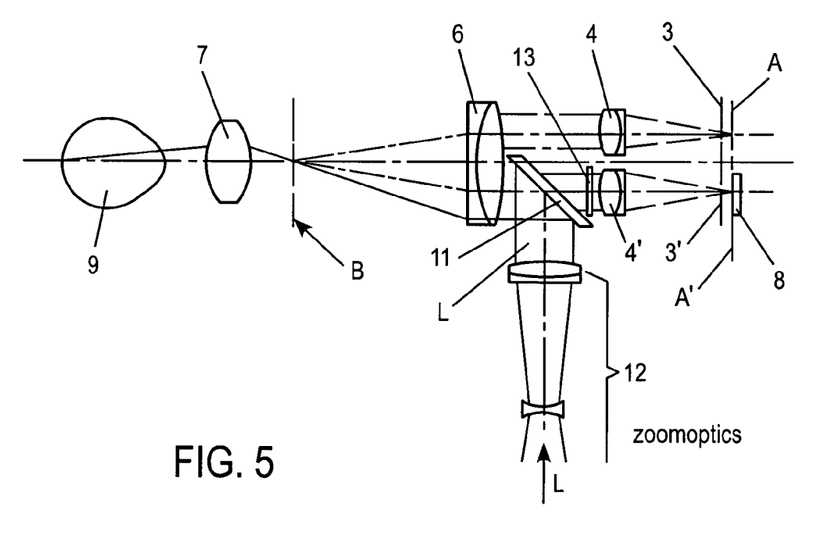
FIG. 5 shows a representation of the reflecting in of a laser behind the ophthalmoscope lens.

FIG. 5 shows the optical coupling in of a therapeutic laser beam L situation, in which the therapeutic laser beam L is coupled in with the aid of a deflection element 11, which is designed as a deflection mirror, only in the longitudinal direction to the observation beam path Bo in the region in which the intermediate focal plane B is imaged to infinity. To prevent the therapeutic laser beam L from reaching the light-sensitive area of the observation unit 8, either the deflection mirror 11 is designed wave-length selective, i.e. not permeable for the wave length of the therapeutic laser or an additional protective filter 13 is placed accordingly in the beam path of the observation beam Bo.

In the same manner, if the protective filter 13 remains stationary, coupling in of the therapeutic laser beam can be carried out via a deflection element 11 placed in the illumination beam path Bl.

Figure 6:
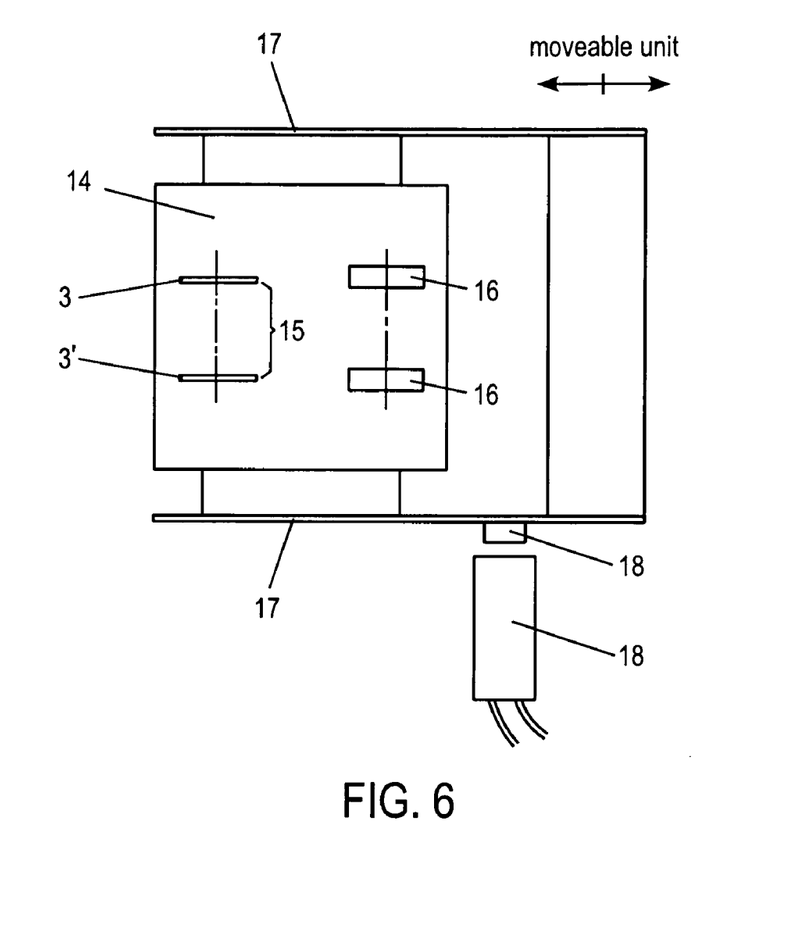
FIG. 6 shows a diaphragm slit arrangement mounted in an oscillating manner, FIG. 7a,b show a representation of the oscillating diaphragm slit.

FIG. 6 shows a schematic representation of the diaphragm slit arrangement 3, 3' mounted in an oscillating manner. The diagram slit arrangement 14 is essentially made of a light-impermeable material, for example a flat metal sheet material which is provided with two pairs of diaphragm slits 15,16 which each have identical diaphragm slit widths respectively. The diaphragm slit arrangement pair 15 has a smaller diaphragm slit width than the diaphragm slit pair 16. The diaphragm slit arrangement 14 is disposed in relation to the illumination beam path and the observation beam path in such a manner that in the depicted preferred embodiment according to FIG. 6, the lower diaphragm slit 3' of diaphragm slit pair 15 oscillates in relation to the observation beam path Bo, whereas the upper diaphragm slit 3 of diaphragm slit pair 15 oscillates synchronously in relation to the illumination beam path Bl. The oscillation procedure of the diaphragm slit arrangement 14, which in the depicted preferred embodiment occurs vertically from top to bottom and conversely, is realized by means of a suited spring bearing 17 which is set into motion in an oscillating manner via a suited induction mechanism 18. In addition, the diaphragm slit arrangement 14 is mounted horizontally movable in such a manner that by means of corresponding lateral movement of the diaphragm slit arrangement, the diaphragm pair 16 is positionable in the respective beam path of the illumination beam path and the observation beam path.

Of particular significance for the applied examination method with which the fundus is analyzed is the vertical oscillating movement discussed in connection with FIG. 6. For instance, if fluorescent angiography, for example indocyanine green angiography, is to be conducted on the to-be-examined fundus, in order to excite the fluorescence, light of great intensity has to be deposited on the fundus.

Figure 7A:
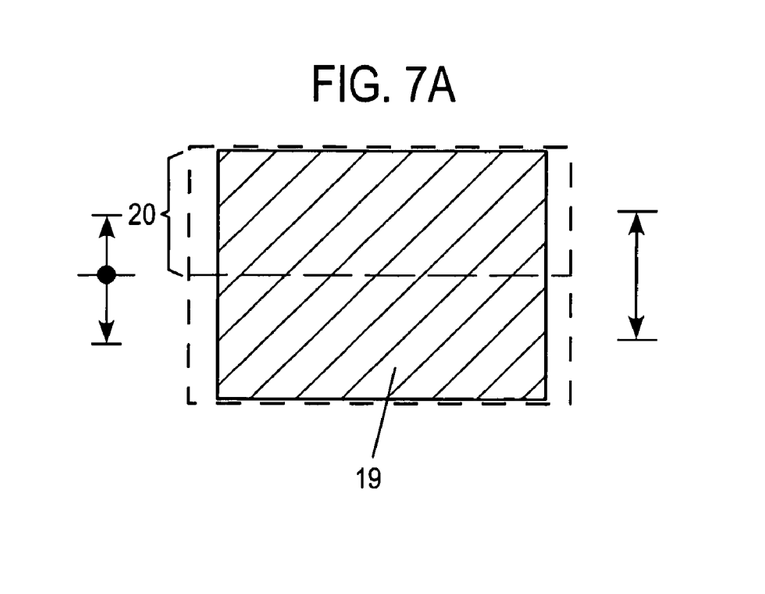

With prior art ophthalmoscopes, light-intensive xenon flash tubes with quick flash generators or powerful illumination lasers, which are technically very complex and very expensive, are employed for this purpose. In contrast to this, conventional halogen lamps, which suffice for taking camera shots of the fundus and are adjustable in brightness, can be used with the invented ophthalmoscope. However, to excite the fluorescence, a diaphragm arrangement is employed whose diaphragm slits are far larger than the usual diaphragm slit dimensions suited for shots of the fundus. Thus, in a particularly advantageous manner, a pair of diaphragm slits, whose single diaphragm slit has a width that preferably is half the length of the light-sensitive area of the observation means along which the diaphragm slit is moved in an oscillating manner, is used for fluorescent angiography in the observation beam path and the illumination beam path. Details are shown in FIG. 7a, in which it is assumed that the light-sensitive area 19 of the CCD sensor along which the diaphragm slit 20 is moved in an oscillating manner according to the arrows is designed rectangular in shape. The oscillating movement of diaphragm 20 in relation to the light-sensitive area 19 occurs in such a manner that the entire width of the diaphragm slit always remains within the light-sensitive area 19, i.e. the returning point of the oscillating movement of the diaphragm slit is selected in such a manner that the width of the diaphragm slit is always within the light-sensitive area 19. In this way, it is ensured that the entire light of the illumination means reflected from the fundus impinges on the light-sensitive area 19 of the observation means, thus ensuring optimum light exploitation and as a consequence obviating the use of expensive light intensive light sources.

Figure 7B:
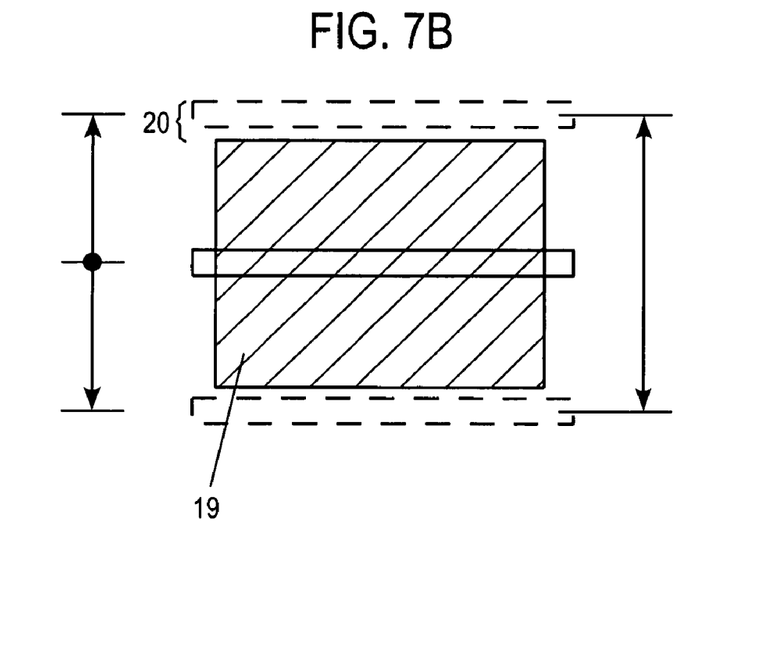

Conversely in the case of fundus observation, the diaphragm slit pair 15 depicted in FIG. 6 is moved in the observation beam path and illumination beam path, whereas according to FIG. 7b the very narrow diaphragm slit 20 is moved in an oscillating manner in such a way in relation to the light-sensitive area 19 that the returning point of the diaphragm slit 20 always lies outside the light-sensitive area 19.

With the aid of the diaphragm arrangement described in the preceding, examinations of the fundus can be conducted as well as fluorescent angiograms can be taken with the aid of a single scanning video ophthalmoscope, thereby opening completely new possibilities and ways of examining the fundus of the eye.

Figure 8A:
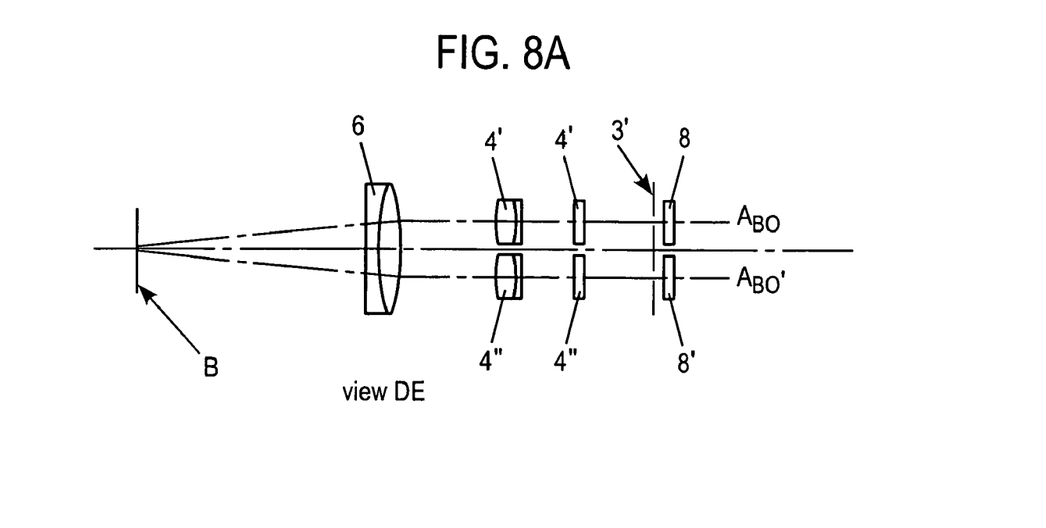
FIGS. 8a-c show a representation of an optical setup of a stereo-ophthalmoscope.
Figure 8B:
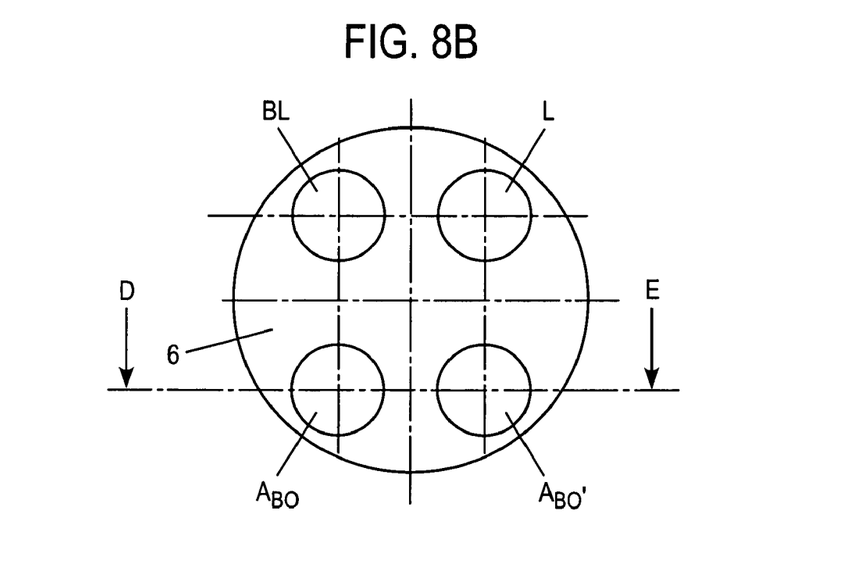

Similarly, the scanning ophthalmoscope designed according to the present invention permits spatially resolved stereoscopic observation of the fundus for spatially resolved diagnosis. When diagnosing the fundus, it is often helpful to obtain stereoscopic images of the fundus, i.e. three-dimensional images. For this purpose, the preferred embodiment according to FIG. 8a, which only shows a sectional representation of the beam paths of the ophthalmoscope, provides two parallel observation beam paths $A_{Bo}$ and $A_{Bo'}$ with the corresponding imaging optics with separate observation means 8 respectively 8'. On the other hand, FIG. 8b shows a cross sectional representation of the optical unit 6 in which all the beam paths of the ophthalmoscope for taking stereoscopic shots are depicted. Thus it may be assumed that the beams of the illumination beam Bl and, for example, an additional coupled-in therapeutic laser beam L are provided in the upper half of the optical unit 6, whereas the two separate observation beam paths $A_{Bo}$ and $A_{Bo'}$ according to FIG. 8a are provided in the lower half.

Figure 8C:
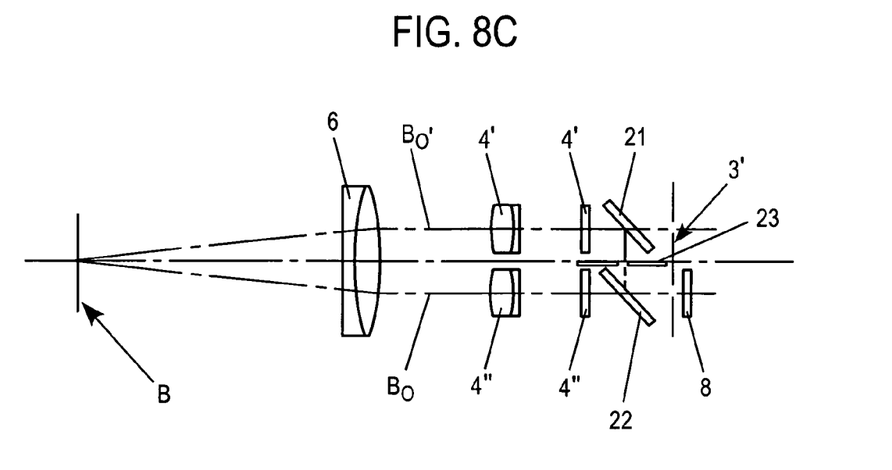

In the same manner, a stereoscopic viewing impression can also be obtained using only a single observation means in that, according to FIG. 8c, the provided two separate observation beam paths Bo and Bo' are deflected via a deflection mirror 21 respectively a splitter mirror 22 onto the observation unit 8. A shutter diaphragm 23 ensures that the images repeatedly changing between the two observation beam paths on the observation means 8 in which the single images coming successively from the two separate observation beam paths Bo, Bo' are brought to concur in a suited manner in order to render a three-dimensional representation. This stereoscopic manner of observation permits improving therapeutic and diagnostic representation of the fundus, but in particular it permits considerably improving therapeutic and diagnostic representation in the front eye medium in comparison to the prior art methods.

Figure 9:
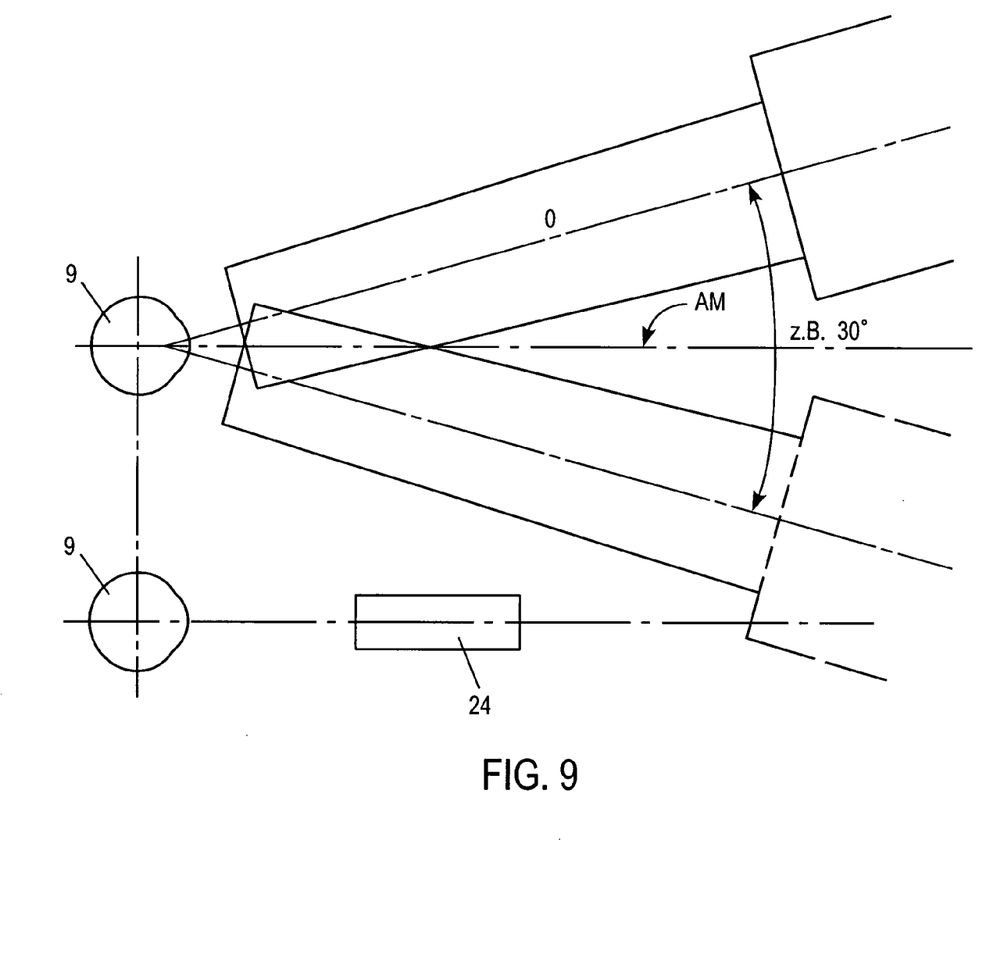
FIG. 9 shows a representation of carrying out a pupil measurement.

Glaucoma examinations require precise analysis, special measurement of the optic nerve knot, the so-called papilla. The papilla is compared with usual reference images and changes in the papilla are documented and evaluated. Obtaining an accurate topographic representation of the papilla requires stereoscopic evaluation of the single images. To obtain stereoscopic images, the ophthalmoscope is turned a defined angle, preferably 30°, in the horizontal plane in relation to the to-be-examined eye. In order that the patient maintains a fixed prescribed viewing direction during both shooting situations, the ophthalmoscope is provided with an optical marking unit 24, which defines a fixed, unchanging viewing direction for the patient independent of the turned position of the ophthalmoscope. FIG. 9 shows a schematic view of such an examination situation.

Let us assume that the drawing plane according to FIG. 9 represents a horizontal plane showing a top view of the to-be-examined eye 9. The ophthalmoscope O is located at a defined distance from the eye 9 and is turnable by a defined, fixed angle, preferably $\beta=30°$, in relation to a central axis AM. In the given shooting position of the ophthalmoscope O, the shots of the fundus are taken, in particular shots of the papilla, which are later combined for stereographic image evaluation. In order to ensure that the patient's eye 9 retains an unchanging viewing direction along the center axis AM during both shooting situations, a marking means 24 indicating the given, fixed viewing direction for the patient depending on the shooting position, is provided at a fixed site on the ophthalmoscope or in the region of the ophthalmoscope.

In combination with the aforedescribed, stereoscopic image evaluation of the papilla for a glaucoma examination, it is also necessary to analyze the papilla hole by way of measuring the depth, thereby permitting exact determination of the volume of the papilla in order to ultimately obtain some indication of the progression of the glaucoma respectively of the cataract.

To do this, it is proposed to move the entire ophthalmoscope spatially resolved or preferably solely the optical unit 6 of the ophthalmoscope longitudinally to the viewing direction in order to obtain in this manner single images from different depth planes as single sectional image shots. Control of altering the position of the optical unit 6 respectively of the entire ophthalmoscope occurs preferably with the aid of a step-by-step motor which conducts the change in position in defined given single steps. The single images taken from individual depth planes are synchronized and composed to a single three-dimensional topographical image of the papilla by means of suited image evaluation software.

Furthermore, the invented ophthalmoscope offers an advantageous combination of diagnostic and therapeutic measures which can be utilized for successful treatment of age-caused macular degeneration (AMD).

In this type degeneration, the barrier between the retina and the pigment and vessel layers lying beneath it is impaired. A vessel-containing neovascular scar grows into the center of the retina and leads to progressive destruction of the photoreceptor, sensory cell layer, which in the worst case can lead to total blindness.

Figure 10A:
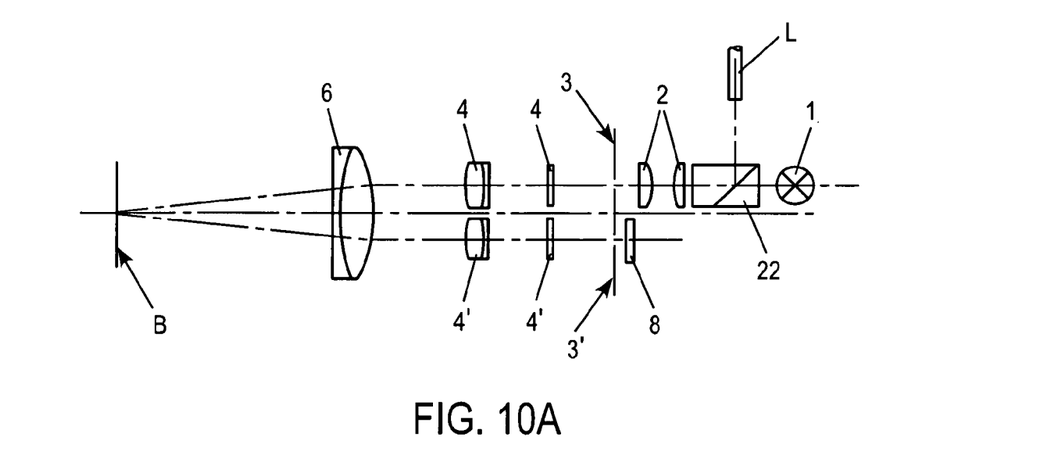
FIG. 10a-c show a representation of conducting an ICG angiography of the fundus and FIG. 11a,b show the placement of a protective filter in the illumination beam path.
Figure 10B:
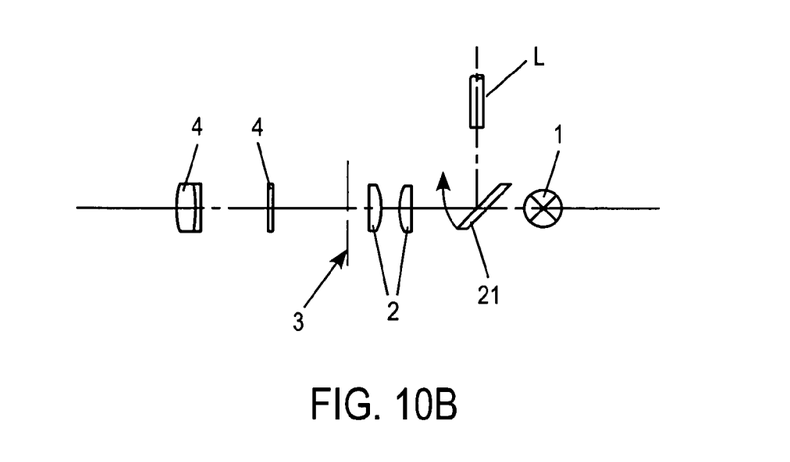

In order to diagnose such type neovacularization, fluorescent (FAG) or indocyanine green (ICG) angiography is conducted which renders the diseased fundus areas or vessels visible with the aid of a dye. To excite the dye, a strong light source, preferably in the blue (FAG) or in the infrared (ICG) spectrum, is required which is able to optically excite the fluorescent dye. According to a preferred embodiment of the ophthalmoscope, a schematic setup of which is shown in FIG. 10a and which essentially is provided with the components previously depicted in FIG. 1, which will not be dealt with in more detail, a beam splitter 22 which couples the light from an emitting laser L, for example having a wavelength of 480 nm or 780 nm, into the observation beam path is provided between the illumination means 1 and the condenser optic 2. As an alternative, according to FIG. 10b, the laser light L can be coupled into the observation beam path via a swingable deflection mirror 21. The latter variant permits alternating the illumination of the fundus using a laser light or light from the light source 1.

In the course of an imminent diagnosis, precise information about the spatial position and size of the neovacularization is obtained with the aid of angiograms. Furthermore, these angiograms serve, by superimposition of shots of a subsequent observation of the fundus, in which suited FAG or ICG shots are made to concur with the image of the fundus utilizing the eye-tracking method, to precisely identify defect, to-be-treated areas of the retina which can be treated with an extended ophthalmoscope arrangement according to FIG. 10c.

Figure 10C:
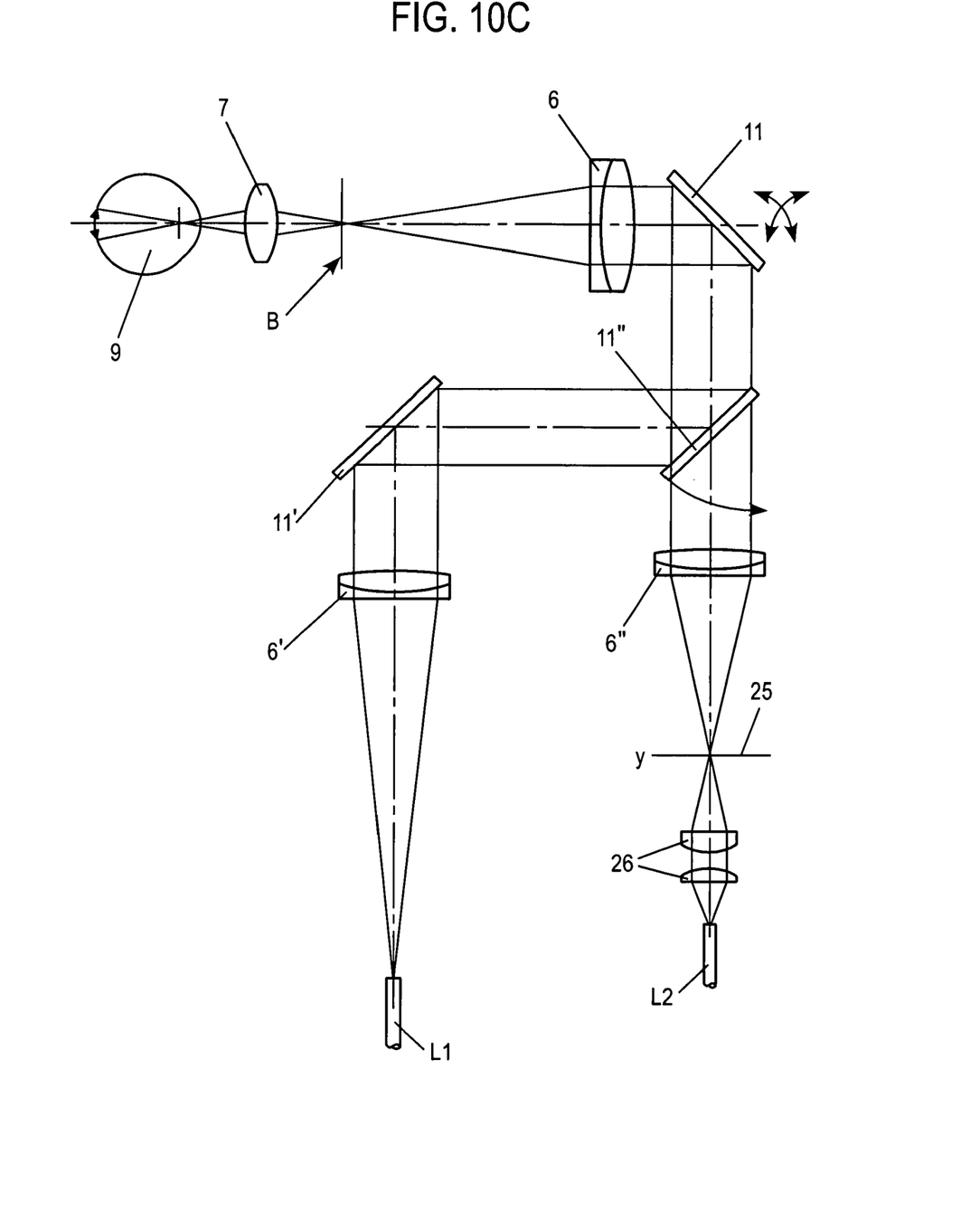

FIG. 10c shows a section of the optic of the ophthalmoscope in whose beam path, in which the intermediate focal plane B is imaged to infinity, a swing mirror 11 is placed. Via the swing mirror 11, two separate laser systems L1, L2, with which immediate treatment of the diagnosed age-caused macular degeneration is possible, can be coupled into the beam path of the ophthalmoscope.

Thus via the deflection mirrors 11', 11", and 11, the light of a therapeutic laser L1 having a wavelength of 810 nm is coupled into the beam path which is focused with a spot size of 50 or 100 μm in diameter on the fundus. With the aid of such a light spot, the tiniest retina areas can be coagulated, thus especially areas in which the so-called "feeder vessels" run which can be considered the cause of AMD developing. The FAG or ICG shots mentioned in the preceding, which are uniformly superimposed on the current fundus using characterizing concurring points, are utilized to locate these areas exactly. To align the laser beam, suited focus target means can be used or suitably designed masks can be placed in the beam path of the laser respectively in the intermediate focal plane B.

Employed to couple the laser beam of laser L1 into the beam path of the ophthalmoscope is, in addition to the mentioned mirrors 11, 11', 11", a lens unit 6' which turns the divergent running laser beam into a parallel beam.

A second laser L2 has the purpose of generating laser radiation with a wavelength of 690 nm which is suited for large area irradiation, for example with a spot size of 400 μm to 6000 μm, of the fundus 9'. Provided in the beam path of laser L2 is an imaging unit 26 which has a focal plane y in which, for example, optical masks 25 are placeable for selective spot design. Iris diaphragms or displays can also be placed in this plane y depending on the suited imaging wishes. Again a lens unit 6" turns the divergent laser beam into a parallel beam for further coupling in.

Figure 11A:
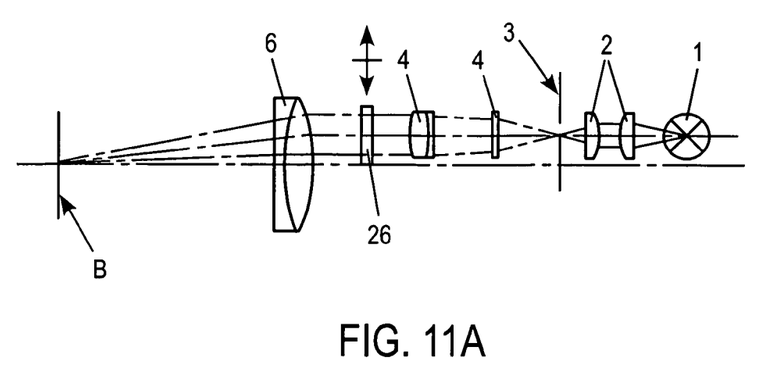
Figure 11B:
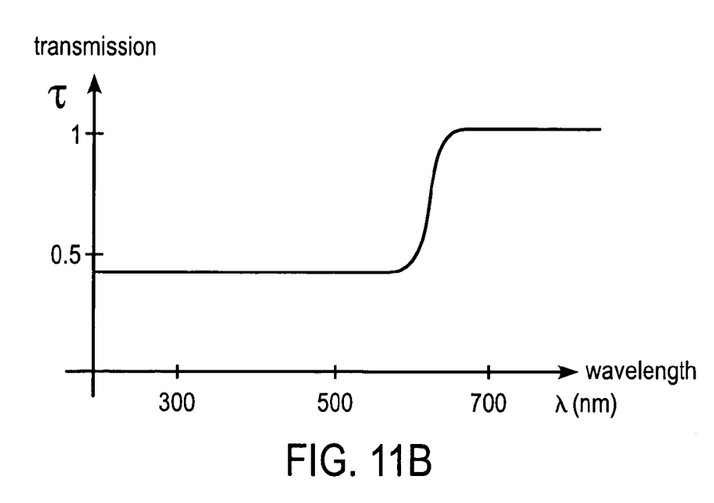

A great advantage in conducting such a treatment to fight diabetes is using a long pass interference filter, preferably a RG 6 filter which possesses constant low transmission in the visible range but lets the infrared portion of the light of the halogen lamp light pass completely. The filter is preferably provided in the illumination beam path before the optical unit 6, due to which the uneasiness of the patient's eye caused by varying brightness can be decreased decisively. Providing such a filter permits reducing the visible light part during laser treatment while at the same time the infrared part of the therapeutic laser and its representation can be fully utilized via the observation means. FIG. 11a shows a schematic representation of a section of this beam path. A preferred transmission diagram of the filter 13 placed in the illumination beam path is shown in FIG. 11b.

LIST OF REFERENCE NUMERALS 1 spot light source in the form of a halogen or xenon lamp
2 2-lens condenser optical system
3 illumination diaphragm
3' observation diaphragm
4 illumination optic
4' observation optic
5 filter arrangement
6 front lens
7 ophthalmoscope lens
8 CCD sensor movable (color-b/w camera)
9 eye
10 group of replaceable components
11 deflection mirror, splitter mirror
12 therapeutic laser adapter
13 protective filter
14 diaphragm arrangement
15 pair of diaphragm slits with small diaphragm slit width
16 pair of diaphragm slits with large diaphragm slit width
17 spring system
18 induction mechanism
19 light-sensitive area of the observation means
20 diaphragm slit
21,22 deflection elements, deflection mirror, beam splitter
23 shutter diaphragm
24 marking means
25 iris diaphragm, display, mask
26 imaging unit
A illumination imaging plane
A' observation imaging plane
AM center axis
B intermediate focal plane, ophthalmoscope lens
F focal lens
L1 therapeutic laser
L2 therapeutic laser

What is claimed is:

1. An ophthalmoscope for examining the fundus of a patient's eye, having
   at least one illumination means, which generates at least one illumination beam, and one imaging optic assignable to said illumination means, said imaging optic imaging said illumination beam onto said fundus of a patient's eye via an intermediate focal plane,
   at least one observation means and an imaging optic assignable to said observation means, said imaging optic imaging an observation beam generated by reflection of said illumination beam at said fundus via said intermediate plane in said observation means, and a diaphragm slit arrangement placed in said illumination beam and said observation beam, said diaphragm slit arrangement having at least one diaphragm slit, respectively, placeable in said illumination beam path and said observation beam path, said diaphragm slits being mounted in a synchronously oscillating manner relative to said illumination beam and said observation beam, wherein said intermediate focal plane is imageable to infinity via at least one optical unit and said intermediate focal plane imaged to infinity is imageable in an imaging plane of said observation beam in which said observation means is provided and said optical unit is provided in the beam path of said observation beam downstream of said intermediate focal plane and is passed through by said illumination beam and said observation beam.

2. The ophthalmoscope according to claim 1, wherein said diaphragm slit arrangement is provided immediately before said imaging plane in the beam direction of said observation beam.

3. The ophthalmoscope according to claim 1, wherein said observation means is a CCD sensor.

4. The ophthalmoscope according to claim 1, wherein said illumination beam passes through said diaphragm arrangement parallel to said observation beam.

5. The ophthalmoscope according to claim 1, wherein an optical imaging unit, which images said fundus in said intermediate plane as well as said illumination beam on said fundus, is provided in the beam path in longitudinal direction of said illumination beam and said observation beam between said patient and said intermediate focal plane.

6. The ophthalmoscope according to claim 5, wherein said optical imaging unit is an ophthalmoscope lens.

7. The ophthalmoscope according to claim 1, wherein said optical unit is at least one achromat.

8. The ophthalmoscope according to claim 1, wherein said optical unit is movable in scaleable steps axially to the observation beam which is directed to infinity.

9. The ophthalmoscope according to claim 1, wherein in longitudinal direction of said observation beam, an optic unit is provided which images said intermediate focal plane imaged to infinity in said imaging plane on said observation means.

10. The ophthalmoscope according to claim 1, wherein in longitudinal direction of said illumination beam, an optic unit is provided, which images said intermediate focal plane imaged to infinity on a uniformly lit area within said imagining plane.

11. The ophthalmoscope according to claim 9, wherein said optic unit in said illumination beam and said optic unit in said observation beam are designed identical in optical effect and/or one-piece.

12. The ophthalmoscope according to claim 1, wherein to said illumination means is assigned an illumination optic, which images said illumination beam at the site of said imaging plane as a uniformly lit area.

13. The ophthalmoscope according to claim 12, wherein said illumination optic is a condenser system.

14. The ophthalmoscope according to claim 1, wherein said illumination beam and said observation beam run parallel in the region of said intermediate focal plane imaged to infinity.

15. The ophthalmoscope according to claim 1, wherein said observation beam and said illumination beam imaged in said intermediate focal plane form an angle $2\alpha$ and the bisecting line of said angle $2\alpha$ runs parallel to the beam path of said illumination beam and said observation beam in the region of said intermediate focal plane imaged to infinity.

16. The ophthalmoscope according to claim 10, wherein said optic units are combinable with a filter unit in longitudinal direction of said observation beams and illumination beams.

17. The ophthalmoscope according to claim 1, wherein at least one group of replaceable optical components moveable longitudinally to said observation beam path and/or said intermediate beam path is placed in said intermediate focal plane.

18. The ophthalmoscope according to claim 17, wherein said group of optical components is a glass plate with markings, a diaphragm arrangement, a filter arrangement and/or a rear projection means.

19. The ophthalmoscope according to claim 1, wherein said diaphragm slit arrangement is provided with at least two pairs of diaphragm slits, of which the diaphragm slits of each said pair of diaphragm slits have identical slit widths and are singly assignable to said illumination beam and said observation beam respectively, the diaphragm slits of at least two pairs of said diaphragm slits have slit widths of different sizes, and the diaphragm slits of said single pairs of diaphragm slits are placeable in said illumination beam and said observation beam respectively by moving said diaphragm arrangement.

20. The ophthalmoscope according to claim 1, wherein in the region of said intermediate focal plane imaged to infinity, a mirror is provided via which an additional beam path, for example a therapeutic laser, can be coupled in longitudinally to said illumination beam and said observation beam.

21. The ophthalmoscope according to claim 1, wherein in the region between said intermediate focal plane and said intermediate focal plane imaged to infinity a mirror is provided via which an additional beam path, for example a therapeutic laser, can be coupled in longitudinally to said illumination beam and/or said observation beam.

22. The ophthalmoscope according to claim 1, wherein a splitter mirror, via which an additional beam path, for example a therapeutic laser, can be coupled into said illumination beam and/or said observation beam, is provided in said region between said intermediate focal plane and said intermediate focal plane imaged to infinity or in said region of said intermediate focal plane imaged to infinity.

23. The ophthalmoscope according to claim 20, wherein said mirror respectively said splitter mirror is designed as a scanning mirror which is swingable about at least two orthogonal spatial axes.

24. The ophthalmoscope according to claim 20, wherein said additional beam path is focusable via said optical unit into said intermediate focal plane.

25. The ophthalmoscope according to claim 1, wherein a fixed, built-in protective filter or a protective filter which can be swing into said observation beam is provided in said observation beam for safeguarding said observation means.

26. The ophthalmoscope according to claim 1, wherein said imaging optic assignable to said illumination means is provided with the following optical components:

an illumination optic unit for imaging said illumination means in said imaging plane, an optic unit, which images the illumination beam emerging from said imaging plane to infinity, an optical unit, which images said illumination beam imaged to infinity on said intermediate focal plane including an optical imaging unit, which images said intermediate focal plane on said fundus of said patient's eye, and said imaging optic assignable to said observation means is provided with the following optical components in the beam direction of said observation beam starting from said fundus of said patient's eye: said imaging unit, which images said fundus onto said intermediate focal plane, said optical unit, which images said intermediate focal plane to infinity, and an optic unit, which images said intermediate plane imaged to infinity in said imaging plane.

27. The ophthalmoscope according to claim 19, wherein said observation means located in said imaging plane is provided with a detector area having a span along which the diaphragm slit assigned to said observation beam oscillates in such a manner that the diaphragm slit of a first pair of diaphragm slits has an oscillation turning point in which said diaphragm slit lies completely outside said detector area, the diaphragm slit of a second pairs of diaphragm slits has an oscillation turning point in which said diaphragm slit lies completely within said detector area.

28. The ophthalmoscope according to claim 27, wherein the slit width of said diaphragm slit of said first pair of diaphragm slits is smaller than the width of the slits of said second pair of diaphragm slits.

29. The ophthalmoscope according to claim 27, wherein the slit width of the diaphragm slits of said first pair of diaphragm slits is smaller than half of the span of said detector area, along which said diaphragm slit oscillates, and the slit width of said diaphragm slits of said second pairs of diaphragm slits is the same size as or larger than half of the span of said detector area.

30. The ophthalmoscope according to claim 1, wherein two spatially separate observation means are provided with corresponding observation beam paths, which spatially separated from each other image said fundus via said intermediate focal plane on the respective observation means via a first and a second imaging optic respectively.

31. The ophthalmoscope according to one claim 1, wherein two spatially separate observation beam paths are provided, which spatially separated from each image said fundus via said intermediate focal plane on a single observation means via a first and a second imaging optic respectively and a splitter optic is provided by means of which said two observation beam paths impinge on said observation means separated from each other, alternately in succession.

32. The ophthalmoscope according to claim 30, wherein said ophthalmoscope is suited for stereoscopic observation of the fundus.

33. The ophthalmoscope according to claim 1, wherein a swing mechanism is provided which swings said ophthalmoscope a given angle from a first position into a second position into a plane intersecting the fundus, and an optical marking unit is provided which defines, independent of the position, an unchanging, site-fixed viewing direction for the patient.

34. The ophthalmoscope according to claim 1, wherein the position of said optical unit can be moved in the longitudinal direction of the observation beam in such a manner that moving said optical unit is measurable.

35. The ophthalmoscope according to claim 34, wherein the position of said optical unit can be movable by means of a step-by-step motor.

36. The ophthalmoscope according to claim 1, wherein a wave-length selective protective filter which can be swung into the illumination beam is provided.

37. The ophthalmoscope according to claim 36, wherein said protective filter largely absorbs visible light and transmits infrared light.

38. The ophthalmoscope according to claim 36, wherein said protective filter is a long pass interference filter.

* * * * *